July 3, 1956 E. F. STOUFFER Plant Pat. 1,494
RASPBERRY PLANT
Filed April 22, 1955
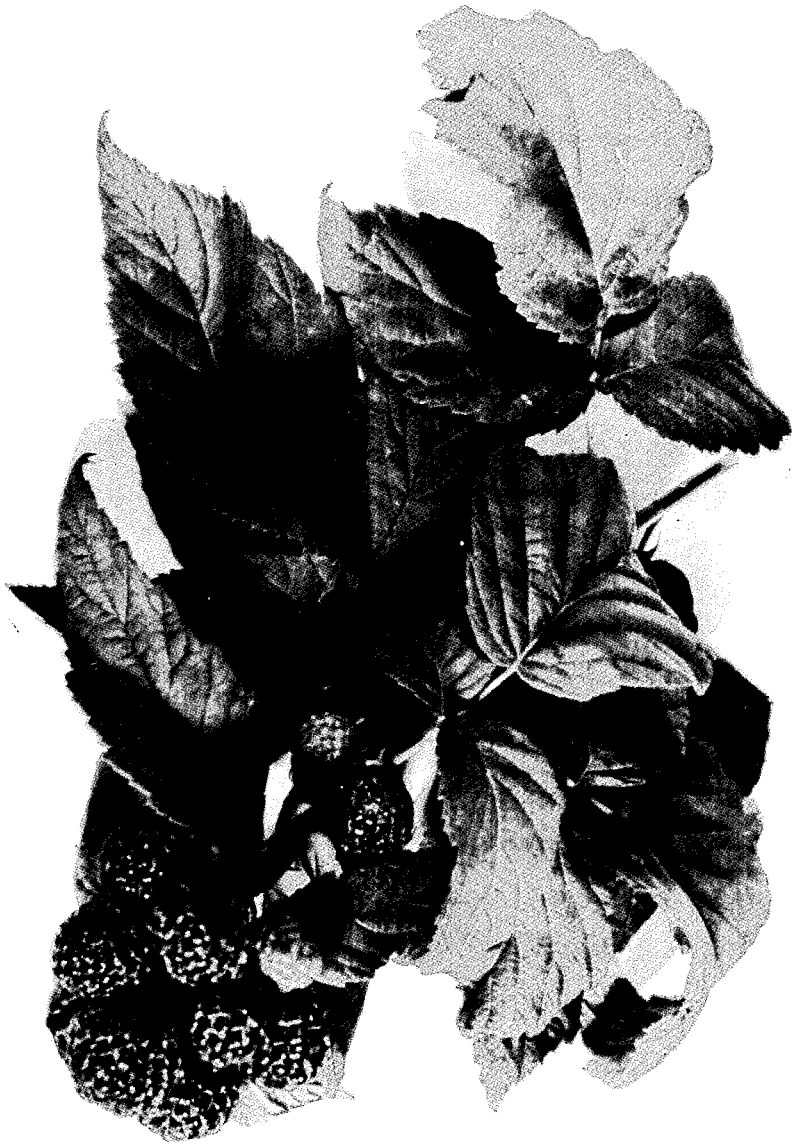
INVENTOR
E. F. Stouffer
By: Robb & Robb
ATTORNEYS.

United States Patent Office

Plant Pat. 1,494
Patented July 3, 1956

1,494

RASPBERRY PLANT

Edwin F. Stouffer, Sterling, Ill., assignor to Stark Bro's Nurseries and Orchards Company, Louisiana, Mo., a corporation of Missouri Application April 22, 1955, Serial No. 503,362

1 Claim. (Cl. 47—62)

The present invention relates to a new and distinct variety of black raspberry plant which was discovered by me as a cultivated seedling on my property at Sterling, Whiteside County, Illinois, said seedling having been originated by open pollination of the well-known variety "Cumberland" (unpatented).

Prolonged tests and observations of my new variety have established that it is definitely distinguished from the "Cumberland" variety by the much larger size and more vigorous growth of the plants, their greater productivity than the "Cumberland" variety, better resistance to hot and dry weather, as evidenced by the fact that my new variety has matured and borne from 2½ to 4 quarts of fruit per plant, while the fruit of "Cumberland" dried up on the canes before maturing, with only a few berries surviving, and the fruit of my new variety is more acid and has a more distinct raspberry flavor than that of "Cumberland." The new variety is also definitely distinguished from all others of which I am aware, and has characteristics which are very desirable and have not been attained in any standard variety with which I am familiar. The following characteristics are particularly outstanding in my new variety, and together represent a unique and desirable combination of features which make my new variety especially useful for both home and commercial use:

(1) The exceptional vigor, productivity and heat resistance of the plant;

(2) The pronounced and delectable flavor of the fruit;

(3) The relatively small seeds in the fruit; and (4) The relatively large size and firmness of the fruit, even under unfavorable weather conditions of high temperatures and lack of moisture.

Asexual reproduction of the new variety by layering, as performed in both Whiteside County, Illinois, and in Pike County, Missouri, shows that the foregoing characteristics and distinctions come true to form and are established and transmitted through succeeding propagations.

The accompanying drawing shows typical specimens of the foliage and fruit of my new variety.

The following is a detailed description of the new variety, with color terminology in accordance with the Horticultural Colour Guide, except where indicated as in accordance with Ridgway's Color Standards and Nomenclature (abbreviated as "Ridgway"):

Parentage: Seedling. Derived from open pollination of "Cumberland."

Propagation: Holds its distinguishing characteristics through succeeding propagations by layering.

Dates first and last picking: June 23–July 3.

(Observations made from specimens grown and tested in Pike County, Missouri.)

Plant:

*Growth.*—Vigorous.

*Root.*—Vigorous.

*Crown.*—Branched; large.

*Leaves.*—Many; medium large. Petiole—medium length; medium stout. Color: Upper surface—Spinach Green, Plate o96o, page 187, vol. 2; lower surface—Spinach Green, Plate o96o/3, page 187, vol. 2. Pubescence—wanting. Leaflets—number—3. Size—central leaflet—3¾ inches x 2⅜ inches; side leaflets—3 inches x 1⅝ inches. Shape—ovate, tapering to an acute point at distal end. Serrations—double; serrations are wide and obtuse, with protruding downwardly hooked point at apex.

*Canes.*—Medium stout; tall. Color — Scheele's Green, Plate 860/3, page 175, vol. 2. Surface—glabrous; no pubescence. Thorns — few. Length—⅛ inch; slightly angled downward. Color—Uranium Green, Plate 63/2, page 63, vol. 1.

Fruit:

*Condition when described.*—Prime (date June 25).

*Size.*—Uniform; large; constant throughout season. Length—⅝ inch. Transverse diameter—13/16 inch.

*Form.*—Rounded truncate; tapering slightly; uniform; flat base; rounded apex.

*Drupelets.*—Medium large (approximately 9/64 inch in diameter); approximately diamond shaped, with definite suture from base for 3/4 of distance to apex; pistils 1/16 inch long and curved back.

*Cavity.*—Wide; deep; funnel-shaped. Color—Pastel Lilac, Plate 437/3, page 128, vol. 2.

*Color.*—Glabrous; Dull Purplish Black, Plate L, Color 65'''', Tone M (Ridgway).

*Receptacle.*—Length ¼ inch. Diameter—3/16 inch. Color—Naples Yellow, Plate 4o3/3, page 121, vol. 2, shading to Chartreuse Green, Plate 663/3, page 90, vol. 1, at base.

*Sepals.*—Acuminate. Number — 5. Length — ⅜ inch. Width at base—⅛ inch. Pubescence—scant. Color—Pod Green, Plate o61/1, page 120, vol. 2.

*Stamens.*—Partly dry at tips when fruit is mature. Length—⅛ inch.

*Fruit stems.*—Radicle ⅝ inch long; very thorny; scant, short pubescence.

*Flesh.*—Juicy; firm. Color (both flesh and juice)—Plum Purple, Plate 934, page 179, vol. 2.

*Seed.*—Size—medium small. Length—about 5/64 inch. Width—1/16 inch. Thickness—1/32 inch. Surface—pitted. Color—Plum Purple, Plate 934, page 179, vol. 2.

*Flavor.*—Subacid; rich.

*Quality.*—Good.

*Shipping quality.*—Good.

*Use.*—Market; canning; freezing; dessert.

Drought resistance: Exceptionally resistant to high temperatures and drought, as determined by comparison with other varieties grown under comparable cultural conditions in Pike County, Missouri.

Soil where grown: Clay loam; well-drained.

Culture: Straw mulch; sprayed only to control mites.

I claim:

A new and distinct variety of black raspberry plant, substantially as herein shown and described, characterized particularly as to novelty by its exceptional vigor, productivity and heat resistance, the pronounced and delectable flavor of its fruit, and by the relatively large size and firmness of its fruit even under unfavorable weather conditions of high temperatures and drought.

No references cited.